(12) United States Patent
Heinonen et al.

(10) Patent No.: US 8,333,191 B2
(45) Date of Patent: Dec. 18, 2012

(54) METHOD AND ARRANGEMENT FOR DETECTING A LEAK IN ANESTHESIA SYSTEM

(75) Inventors: Erkki Paavo Heinonen, Helsinki (FI); Tom Jakob Haggblom, Vantaa (FI)

(73) Assignee: General Electric Company, Schenectady, NY (US)

( * ) Notice: Subject to any disclaimer, the term of this patent is extended or adjusted under 35 U.S.C. 154(b) by 563 days.

(21) Appl. No.: 12/565,019

(22) Filed: Sep. 23, 2009

(65) Prior Publication Data
US 2010/0078018 A1    Apr. 1, 2010

(30) Foreign Application Priority Data
Sep. 26, 2008   (EP) .................................... 08396014

(51) Int. Cl.
*A61M 16/00*        (2006.01)
(52) U.S. Cl. ......... 128/203.14; 128/200.24; 128/202.22; 128/203.12; 128/203.15
(58) Field of Classification Search .......... 128/200.11–200.24, 203.12–203.28, 128/910
See application file for complete search history.

(56) References Cited

U.S. PATENT DOCUMENTS

| | | | | |
|---|---|---|---|---|
| 5,094,235 | A | * | 3/1992 | Westenskow et al. ... 128/204.22 |
| 5,161,525 | A | | 11/1992 | Kimm et al. |
| 5,497,767 | A | * | 3/1996 | Olsson et al. ............. 128/205.13 |
| 5,509,406 | A | * | 4/1996 | Kock et al. ............... 128/203.14 |
| 5,651,360 | A | | 7/1997 | Tobia |
| 5,730,119 | A | * | 3/1998 | Lekholm ................... 128/200.24 |
| 5,771,882 | A | * | 6/1998 | Psaros et al. ............. 128/203.12 |
| 5,806,513 | A | * | 9/1998 | Tham et al. ............... 128/204.22 |
| 5,857,458 | A | | 1/1999 | Tham et al. |
| 8,033,280 | B2 | * | 10/2011 | Heinonen ................ 128/204.22 |
| 2009/0090359 | A1 | * | 4/2009 | Daviet et al. ............. 128/203.14 |

FOREIGN PATENT DOCUMENTS

| | | |
|---|---|---|
| EP | 1961439 | 8/2008 |
| WO | 9806449 | 2/1998 |
| WO | 2006137784 | 12/2006 |

* cited by examiner

*Primary Examiner* — Annette Dixon
(74) *Attorney, Agent, or Firm* — Global Patent Operation

(57) ABSTRACT

A method and arrangement for detecting a leak in an anesthesia system. The method includes controlling respiratory movements by means of ventilator gas flows and measuring the ventilator gas flow added for an inspiration and removed for an expiration. The method also includes supplying a fresh gas flow for a respiration and measuring the fresh gas flow added for the respiration. The method further includes receiving information indicative of the measured gas flows, determining based on said received information both the gas volume added and the gas volume removed and comparing these determined gas volumes to each other. The method also includes determining based on comparing the anesthesia system leakage.

13 Claims, 2 Drawing Sheets

METHOD AND ARRANGEMENT FOR DETECTING A LEAK IN ANESTHESIA SYSTEM

CROSS-REFERENCE TO RELATED APPLICATIONS

This application claims priority under 35 U.S.C. §119(a)-(d) or (f) to prior-filed, co-pending European patent application serial number 08396014.6, filed on Sep. 26, 2008, which is hereby incorporated by reference in its entirety.

STATEMENT REGARDING FEDERALLY SPONSORED RESEARCH OR DEVELOPMENT

Not Applicable

NAMES OF PARTIES TO A JOINT RESEARCH AGREEMENT

Not Applicable

REFERENCE TO A SEQUENCE LISTING, A TABLE, OR COMPUTER PROGRAM LISTING APPENDIX SUBMITTED ON COMPACT DISC

Not Applicable

BACKGROUND OF THE INVENTION

1. Field of the Invention

This disclosure relates generally to a method and an arrangement for detecting a leak in an anesthesia system.

2. Description of Related Art

Inhalation anesthesia is delivered using a re-breathing circuit comprising an inspiratory limb through which a patient gets an inspired breathing gas from a ventilator, an expiratory limb carrying an exhaled gas back to the ventilator, a Y-piece connecting the inspiratory and expiratory limbs to a further patient limb providing a gas communication pathway to patient lungs. An expired gas comprises a lot of expensive and environment-hostile anesthesia gases. The re-breathing circuit is used to return the expired gas to next inspiration. Before doing this, the gas must be cleared out from the carbon dioxide extracted from the patient lungs as waste product of a patient metabolism. The clearance is done in a $CO_2$ absorber.

Traditional anesthesia ventilator comprises a bellows-in-bottle, which separates a ventilator drive gas from the circulating breathing gas. For the inspiration, outside of the bellows is pressurized with ventilator drive gas. This squeezes the bellows forcing the breathing gas within the bellows to flow towards the patient lungs. During the expiration, the drive gas pressure is released and the gas pressurized in the patient lungs flows out filling the bellows. Breathing gas is supplied to the re-breathing circuit as continuous flow using a fresh gas line. Once the bellows is filled, further gas flow to the circuit from the patient and the fresh gas line increases the circuit pressure that opens an over-pressure bleed valve for a removal of this further gas to a scavenging system.

An inspiration gas volume is controlled using a flow sensor measuring either the ventilator drive gas or the patient inspiration gas depending on the application. Measuring the drive gas excludes the fresh gas delivered to the circuit and the resulting breath volume would be larger by this fresh gas flow compared to the delivered drive gas volume. Measuring the patient inspiration gas flow includes both the ventilator drive gas induced flow from the bellows and the fresh gas flow. In some systems the ventilator drive gas is also compensated for the fresh gas flow in a way to reduce ventilator drive gas flow with increasing fresh gas flow.

The expiration gas volume is not controlled. The volume that is inspired is passively expired during following expiration. Some systems, however, are equipped to measure also expired gas flow for monitoring purposes. This is done with a flow sensor connected to the expiratory limb.

A breathing circuit tightness is essential for the successful patient ventilation. Leakages occur frequently because the breathing circuit is disassembled for cleaning and reassembled between patients. This assembly procedure may be complicated and is liable for errors causing leakages. Therefore, all anesthesia machines enclose a breathing circuit leak test that is performed before the patient is connected and the operation begins. However, circuit modifications, disconnections, and reconnections are needed every now and then for various reasons like a patient suction also during an operation. Also an endotrahceal tube sealing may loose, or inadvertent loosening of some tubing may occur in the busy and often tight anesthesia environment. These are not revealed by the pre-use leak test.

Anesthesia clinicians favor the bellows-based re-breathing circuit because the end-expiratory position of the bellows visualizes a circuit leak. Would the breathing gas leak out from the re-breathing circuit be larger than the compensatory fresh gas flow rate, the bellows does not rise to its full extent. As a leak indicator this is, however, not very sensitive, since the leak must be larger than the fresh gas flow rate, which may be anything from 0.5 to 6 L/min. Further disadvantage of the bellows-based system is that if the bellows gets empty due to insufficient leak to the fresh gas flow—ratio, there is no gas for the patient breathing and the patient ventilation stops.

In a new re-breathing circuit a drive gas—a breathing gas separation is done using a long gas channel where a gas column is moving back-and-forth during the course of the inspiration and the expiration. As an advantage, such system does not have any volume limitation and even in leak situations the patient breathing volume can be delivered. Also here, however, the leak visualization is lost.

BRIEF SUMMARY OF THE INVENTION

The above-mentioned shortcomings, disadvantages and problems are addressed herein which will be understood by reading and understanding the following specification.

In an embodiment, a method for detecting a leak in an anesthesia system includes controlling respiratory movements by means of ventilator gas flows and measuring the ventilator gas flow added for an inspiration and removed for an expiration. The method for detecting a leak in an anesthesia system also includes supplying a fresh gas flow for a respiration and measuring the fresh gas flow added for the respiration. The method for detecting a leak in an anesthesia system further includes receiving information indicative of the measured gas flows and determining based on the received information both the gas volume added and the gas volume removed. The method for detecting a leak in an anesthesia system also includes comparing these determined gas volumes to each other and determining based on comparing the anesthesia system leakage.

In another embodiment, an arrangement for detecting a leak in an anesthesia system includes a ventilator configured to control respiratory movements, including at least one flow sensor for measuring a ventilator gas flow added for an inspiration and removed for an expiration and a gas mixer for supplying a fresh gas flow for a respiration, including at least one flow sensor for measuring the fresh gas flow added. An arrangement for detecting a leak in an anesthesia system also includes a breathing circuit for conducting an expiration gas flow to the ventilator and for conducting the fresh gas flow from the gas mixer for the respiration and for conducting the ventilator gas flow added for the inspiration. An arrangement for detecting a leak in an anesthesia system further includes a leak analyzer for receiving information indicative of the measured gas flows of the flow sensors and which leak analyzer is configured to determine based on the information both the gas volume added and the gas volume removed and to compare these gas volumes to each other and to determine the anesthesia system leakage.

In yet another embodiment an arrangement for detecting a leak in an anesthesia system includes a ventilator configured to control respiratory movements, including at least one flow sensor for measuring a ventilator gas flow for an inspiration and for an expiration when gas is removed and a gas mixer for supplying a fresh gas for a respiration, including at least one flow sensor for measuring the fresh gas flow. An arrangement for detecting a leak in an anesthesia system also includes a breathing circuit for conducting an expiration gas flow to the ventilator and for conducting the fresh gas flow from the gas mixer for the respiration and for conducting the ventilator gas flow added for the inspiration and which breathing circuit includes a patient flow sensor for measuring a total gas flow of the inspiration and expiration. An arrangement for detecting a leak in an anesthesia system further includes a leak analyzer for receiving information indicative of the measured gas flows of the flow sensors and which leak analyzer is configured to determine based on the information both the gas volume added and the gas volume removed and to compare these gas volumes to each other and to determine whether or not they are substantially equal and in case equal proving that the anesthesia system is tight or in case non-equal proving a leak in the system is detected.

Various other features, objects, and advantages of the invention will be made apparent to those skilled in art from the accompanying drawings and detailed description thereof.

BRIEF DESCRIPTION OF THE SEVERAL VIEWS OF THE DRAWINGS

Reference is now made briefly to the accompanying drawings, in which.

DETAILED DESCRIPTION OF THE INVENTION

Specific embodiments are explained in the following detailed description making a reference to accompanying drawings. These detailed embodiments can naturally be modified and should not limit the scope of the invention as set fort in the claims.

Figure 1:
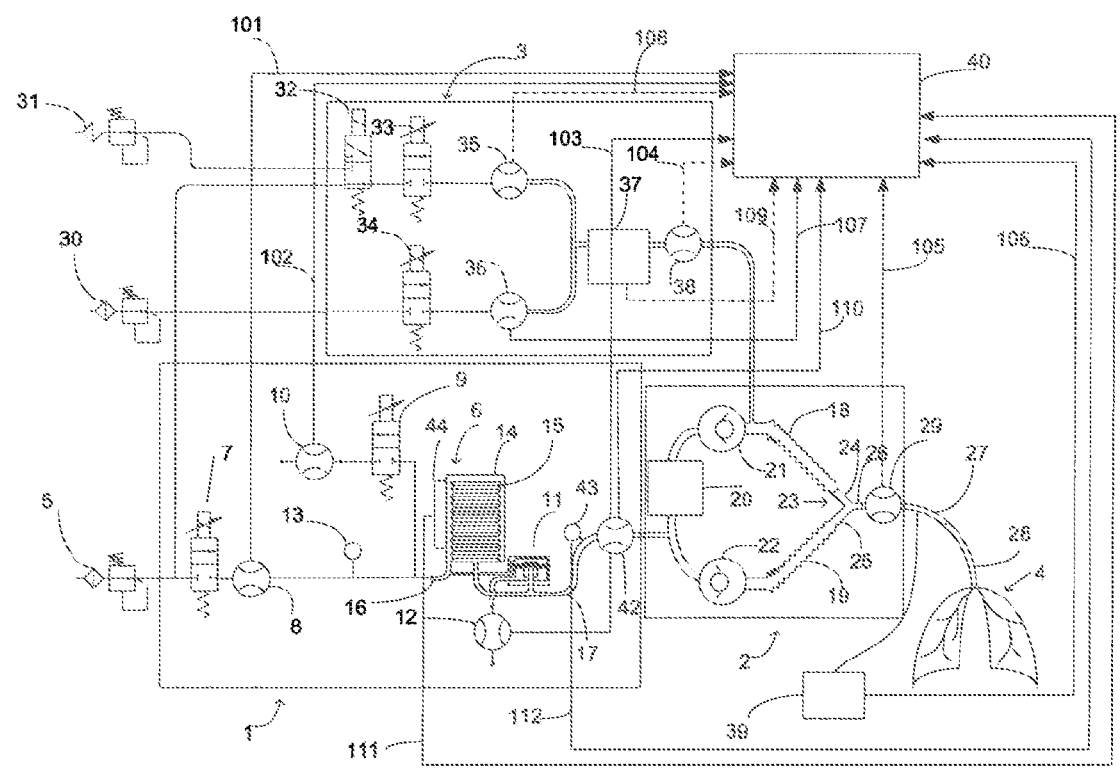
FIG. 1 is a schematic view of a system in accordance with an embodiment.
Figure 2:
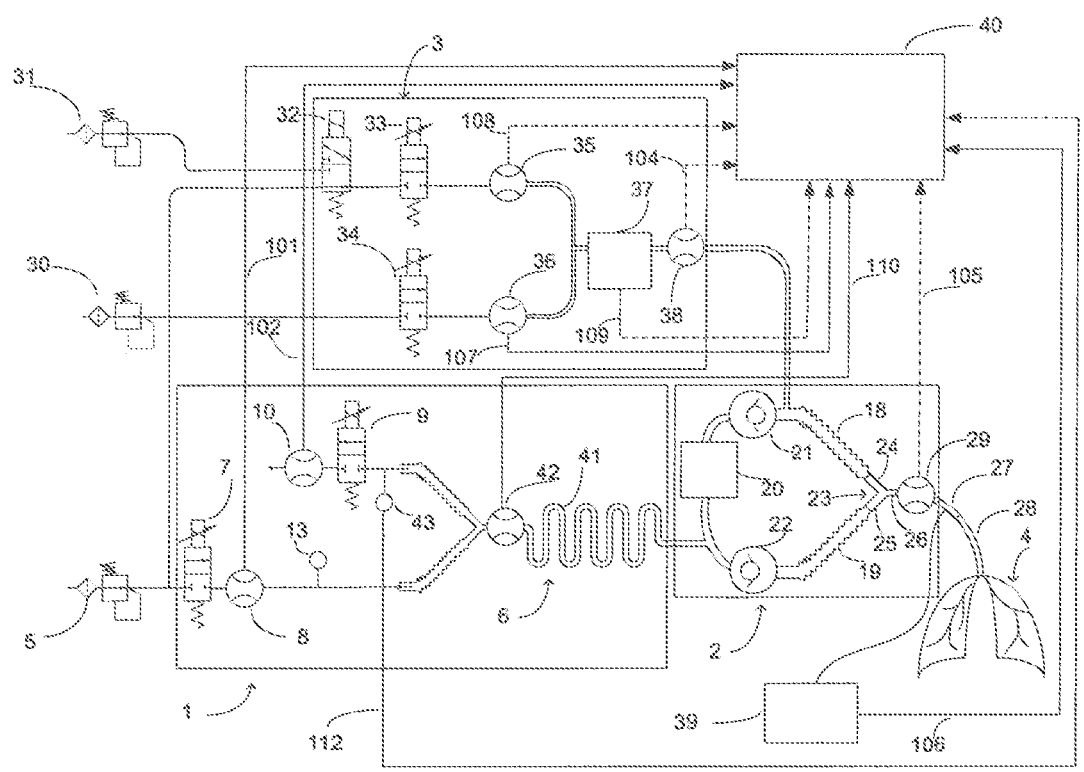
FIG. 2 is a schematic view of a system in accordance with another embodiment.

FIGS. 1 and 2 shows an arrangement for detecting a leak in an anesthesia system. Also a method for detecting a leak in an anesthesia system is disclosed. The anesthesia system comprises a ventilator 1, a breathing circuit 2, a fresh gas mixer 3 and a leak analyzer 40. A subject 4 is connected to the breathing circuit 2 by means of an endotracheal tube 28. According to an embodiment, measuring differences in a gas volume delivered into the breathing circuit 2 during an inspiration and removed from the breathing circuit 2 identifies a leak. Such leak detection requires sensors for a fresh gas flow, a ventilator gas flow for the inspiration, a ventilator gas flow for the expiration, and a scavenged gas flow. The gas volume removed during the expiration lagging the inspired gas volume indicates the leak. The difference of these two gives also the magnitude of this leak, and as such reveals a leakage independently of the fresh gas flow.

In FIG. 1 the ventilator 1 is connected to a gas supply 5, which is typically pressurized air or sometimes also oxygen. The ventilator 1 comprises a reciprocating unit 6 for compressing gas towards lungs of the subject to facilitate the inspiration, a flow control valve 7 to control the inspired gas flow from the gas supply 5 towards the reciprocating unit 6, a flow sensor 8 such as a driving gas inspiration flow sensor for measuring a ventilator gas flow added for the inspiration, which flow sensor typically locates between the flow control valve 7 and the reciprocating unit 6. Further the ventilator 1 comprises an expiration valve 9 used to control the expired gas flow rate releasing the gas of the ventilator 1 when the subject 4 is expiring, a flow sensor 10 such as an expiration flow sensor for measuring a ventilator gas flow removed for the expiration through the expiration valve 9. The ventilator 1 can also comprise a scavenging valve 11 allowing an extra expired gas of the subject 4 to leave the breathing circuit 2 and a flow sensor 12 for measuring a ventilator gas flow removed for the expiration through the scavenging valve 11. Very often the ventilator 1 also comprises a ventilator pressure sensor 13 to measure a pressure of the ventilator gas upstream the reciprocating unit 6 and the ventilator 1 may be equipped with a gas supply selection (not shown) that can be used to switch the ventilator gas flow for the inspiration either manually or automatically e.g. in case the used gas gets un-pressurized. The reciprocating unit 6 shown in FIG. 1 comprises a bottle 14 and a bellows 15 within the bottle 14 for controlling respiratory movements of the subject's lungs. There is also shown a sensor 44 for indicating a position of the bellows 14 and especially to indicate whether or not the bellows is rising up to a top of the bottle 14.

A gas flow added for the inspiration and measured by the flow sensor 8 of the ventilator 1 and regulated with the flow control valve 7 is controlled according to a control algorithm embedded in a controller device (not shown). An output of the flow sensor 8 as well as a signal of the ventilator pressure sensor 13 can be used to control the inspiration flow. The expiration flow measured by the flow sensor 10 is controlled with expiration valve 9. When ventilating the patient, the expiration valve 9 is closed and the flow control valve 7 is opened for the inspiration flow. This flow fills the bottle 14 making the bellows 15 to push down pushing the gas within the bellows further towards the subject 4. During the expiration the flow control valve 7 is closed and the expiration valve 9 is opened to control the expiration flow and pressure. The gas pressurized in the bottle 14 is released allowing the gas from lungs to fill the bellows 15 up. When the bellows 15 is filled, it hits the top of the bottle 14, and the further gas flow into the system increases the pressure within the bellows 15. When this pressure exceeds the bottle pressure, the scavenging valve 11 will open allowing the further gas flow to scavenging system and which flow is measured with the flow sensor 12. The flow sensor 8, the flow sensor 10 and the flow sensor 12 are presented separately for simplicity. However, the flow sensor 8 and the flow sensor 10 could be combined to a single sensor connected at an outlet 16 of the bottle 14 so that this sensor could measure both the inspired and expired gas flow. Alternatively the expired gas flows measured by the flow sensor 10 and the flow sensor 12 could be combined and measured with a single flow sensor. As a further alternative another flow sensor 42 may be connected to a ventilator tube 17 where the reciprocating flow can be measured with single sensor to both directions. This sensor would replace all of the flow sensors 8, 10, and 12, but is not capable to identify the leak occurring in the reciprocating unit 6 or scavenging valve 11.

The ventilator 1 is connected to the breathing circuit 2 such as a re-breathing circuit by means of the ventilator tube 17 for both inspired and expired gas flows. The breathing circuit 2 comprises an inspiration tube 18 for inspired gas, an expiration tube 19 for expired gas, a CO2 remover 20 such as CO2 absorber to remove or absorb carbon dioxide from the exhaled gas coming from the subject 4, a first one way valve 21 for inspired gas in the inspiration tube 18, a second one way valve 22 for expired gas in the expiration tube 19, a branching unit 23 such as a Y-piece having at least three limbs, one of them being an inhalation limb 24 for inspired gas, a second one being an expiration limb 25 for expired gas, a third one being a combined inspiration and expiration limb 26 for both inspired and expired gases. The inhalation limb 24 is connectable to the inspiration tube 18 and the expiration limb 25 is connectable to the expiration tube 19. The combined inspiration and expiration limb 26 of the branching unit 23 may be connectable by means of a patient tube 27 to the endotracheal tube 28 allowing the gas exchange with airways of the subject 4.

The amount of gas removed from the breathing system due to the absorption of CO2 in the CO2 remover 20 is typically between 100-200 L/min. With sufficient accuracy of leak quantification this CO2 removal can be estimated as constant. Alternatively that can be estimated using the fresh gas flow, minute ventilation, and measured expired CO2 concentration.

The gas removed by the subject in breathing is mostly oxygen and temporarily in minor amounts adjoining to changes in the breathing gas concentration also the other breathing gases. The oxygen removal is typically between 150-250 L/min. This is more or less compensated with the CO2 produced by the subject to the breathing system. The CO2 production and O2 consumption can be measured using gas analyzer and taken into consideration in the leak analyzer, but because their values correspond each other the gas exchange of the subject can be omitted when analyzing the circuit leak.

At the end of the expiration when the flow rate from the subject 4 is reduced close to zero the breathing circuit pressure is constant and equal to the pressure within the reciprocating unit 6. This pressure is measured with a pressure sensor 43 and because of the constancy of the pressure the pressure sensor 43 can be connected in any appropriate place in the circuit. Thus the pressure sensor 43 can locate besides in the ventilator 1 as shown in FIG. 1, but also in other parts of the anesthesia system e.g. in the breathing circuit 2 or in the patient limb 27. Change in positive end-expiratory pressure (PEEP) between breaths indicates a change in anesthesia system, including the breathing circuit, reciprocating unit, and the subject lung, volume. If the anesthesia system compliance is known, the change in volume can be calculated as the product of ΔPEEP and the system compliance. Otherwise the change in PEEP can be used qualitatively to prevent leakage identification. PEEP adjustment is normal clinical therapy action taken in order to optimize gas exchange and preserve the lungs While increasing the pressure the volume of the anesthesia system is increasing because of the increased lung volume and vice versa while decreasing the pressure the volume of the anesthesia system is decreasing because of the decreased lung volume. By adjusting the positive end-expiratory pressure a user or even the ventilator itself, if so desired, can control the lungs' function.

The inspiration gas flows from the reciprocating unit 6 through the ventilator tube 17, the CO2 remover 20 and the inspiration tube 18 of the patient circuit 2 to the branching unit 23 and further through the patient tube 27 and the endotracheal tube 28 to the lungs of the subject 4. The second one-way valve 22 on the expiratory tube 19 guides the gas flow direction to the inspiration tube 18 by closing the flow from the ventilator tube 17 through the expiration tube 19. Increasing the gas volume within the lungs increases the lung pressure due to the lung compliance. Once the inspiration stops and the expiration valve 9 opens relieving the bottle 14 pressure, the lung compliance pushes the alveolar gas through the endotracheal tube 28 and the patient tube 27 to the branching unit 23 and further through the expiration tube 19 and the ventilator tube 17 to fill the bellows 15. The patient tube 27 may be equipped also with a patient flow sensor 29 measuring the reciprocating inspiration- and expiration flows.

The gas mixer 3 for delivering a fresh gas is connected to the breathing circuit 2. The gas mixer 3 is used to compose the patient breathing gas. One or more gas supplies 5, 30, 31 is connected to the gas mixer 3. The gas supply 5 is for the air as described above, the gas supply 30 is for oxygen and the gas supply 31 is for nitrous oxide. The gas mixer comprises a selector valve 32 to select either the gas supply 31 for nitrous oxide or the gas supply 5 for air, a flow regulating valve 33 for regulating either nitrous oxide or air flow, a flow regulating valve 34 for regulating oxygen flow and an anesthetic agent supply 37 such as a vaporizer for supplying anesthetic agent to anesthetize the subject 4. The gas mixer 3 also comprises one or more flow sensors 35, 36, 38 for measuring the fresh gas flow added into the anesthesia system for respiration. The flow sensor 35 downstream the flow regulating valve 33 may be adapted to measure either nitrous oxide or air flow as a fresh gas, the flow sensor 36 downstream the flow regulating valve 34 may be adapted to measure oxygen flow as a fresh gas. The mixture is then further guided to the anesthetic agent supply 37 in case it is a vaporizer for adding the inhalation agent into the mixture as shown in FIG. 1. Alternatively the gas mixer 3 may be equipped with a flow sensor 38 for measuring the total gas flow of the gas mixer 3, but it is not absolutely necessary, because the total gas flow of the gas mixer 3 can be determined from other available information. If there is no flow sensor 38 downstream the anesthetic agent supply 37 the vaporized inhalation agent flow can either be measured by the anesthetic agent supply 37 itself or it is known gas flow in which case it can be based on a concentration setting of this anesthetic agent supply 37.

Alternatively the anesthesia agent can be injected directly into the breathing circuit in a liquid form when it will be vaporized to the gas in the circuit or as a vapor. In both cases the gaseous amount of the injected agent need to be communicated to the leak analyzer 40. As a further alternative in an intravenous anesthesia the anesthesia gas may not be used at all when the implication to added gas volume is zero.

The breathing circuit 2 may still be completed with a gas analyzer 39, which can be of a side-stream type as presented or a mainstream type. Side-stream analyzers take a sample gas flow for analysis from the breathing circuit 2. This sample gas flow is 50-250 mL/min depending on the analyzer. The gas analyzer 39, which is the mainstream type is analyzing the flowing gas directly in the breathing circuit 2 or in the patient tube 27.

The leak analyzer 40 includes a processing unit to make determinations based on the information collected from the anesthesia system. The leak analyzer 40 is connected through a signal line 101 to the flow sensor 8 of the ventilator 1, which signal line 101 is adapted to carry a signal from this flow sensor 8 to the leak analyzer 40. Also the leak analyzer 40 is connected through a signal line 102 to the flow sensor 10 of the ventilator 1, too, which signal line 102 is adapted to carry a signal from this flow sensor 10 to the leak analyzer 40. Further the leak analyzer is connected through a signal line 103 to the flow sensor 12 of the ventilator 1, which signal line 103 is adapted to carry a signal from this flow sensor 12 to the leak analyzer 40. Also the leak analyzer 40 is connected through a signal line 104 to the flow sensor 38 of the gas mixer 3, which signal line 104 is adapted to carry the fresh gas flow signal from this flow sensor 38 to the leak analyzer 40. This leak analyzer 40 is advantageously connected through a signal line 105 to the patient flow sensor 29, which signal line 105 is adapted to carry a signal from the patient flow sensor 29 to the leak analyzer 40. The leak analyzer 40 may also be connected through a signal line 106 to the gas analyzer 39, which signal line is adapted to carry a sample gas flow signal from the gas analyzer 39 to the leak analyzer 40. In case the signal line 104 between the flow sensor 38 and the leak analyzer 40 does not exist, this can be compensated by a signal line 107 between the flow sensor 36 and the leak analyzer 40, a signal line 108 between the flow sensor 35 and the leak analyzer 40 and a signal line 109 between the anesthetic agent supply 37 and the leak analyzer 40. The signal line 109 is needed in inhalation anesthesia using the anesthetic agent supply 37. Also the sensor 44 for indicating the position of the bellows 15 is connected through a signal line 111 to the leak analyzer 40 to carry a signal. The pressure sensor 43 for measuring the pressure of the breathing circuit is connected through a signal line 112 to the leak analyzer 40.

The leak analyzer 40 is adapted to receive from the different flow sensors an information indicative of the measured gas flows, which may mean that the information is the measured gas flow or some other information like a gas volume information based on the gas flow measurement. Thus the leak analyzer 40 does not necessarily make calculations from the gas flow information to the gas volume information, but naturally may be able to do that.

Using the inspiration flow signal of the signal line 101 from the flow sensor 8 of the ventilator 1 the leak analyzer 40 according to one embodiment determines the inspiration volume due to the gas flow from the gas supply 5 and using the expired gas flow sensor signal of the signal line 102 from the flow sensor 10 of the ventilator 1 the leak analyzer 40 determines the expired gas volume. Using the scavenging flow signal of the signal line 103 from the flow sensor 12 of the ventilator 1 the leak analyzer 40 can determine how much gas is removed from the breathing circuit 2 during the respective breath cycle. The amount of the fresh breathing gas delivered into the breathing circuit 2 during the breath cycle is determined using the flow sensor signal of the signal line 104 received from the flow sensor 38 of the gas mixer 3, and the amount of the breathing gas removed by the gas analyzer 39 is determined from the signal of the signal line 106. The signal of the gas analyzer 39 may come e.g. from its own flow sensor (not shown) or the signal simply is an information of the known gas flow through the gas analyzer 39. The signal from the gas analyzer 39 is not needed in case the gas sample withdrawn is returned to the breathing circuit 2 or in case the gas analyzer is of a mainstream type wherein the gas is not withdrawn to the gas analyzer 39.

From the determined information, which can be volumes, the leak analyzer 40 then finally is adapted to determine both the gas volume added and the gas volume removed during the breath cycle and is adapted to compare these determined gas volumes to each other and the change in the gas volume stored in the anesthesia system and is adapted to determine based on the comparison the anesthesia system leakage. The anesthesia system is leaking in case the gas volume added and the gas volume removed are substantially non-equal and the anesthesia system is tight in case the gas volume added and the gas volume removed are substantially equal. Typically the anesthesia system is leaking in case the gas volume added is substantially larger than the gas volume removed compared to the change in the amount of gas stored in the anesthesia system and the anesthesia system is tight in case the difference in the gas volume added and the gas volume removed are substantially equal compared to the change in the amount of gas stored in the anesthesia system. According to one embodiment the gas volume added and the gas volume removed are substantially equal in case the difference of the gas volumes is less than 250 ml/min, but preferably it should be less than 100 ml/min. Similarly they are substantially non-equal in case the difference in gas volumes is more than 250 ml/min and preberably more than 100 ml/min. Identification of the leak may also be trigger with increasing leak rate either notification, warning, or alarm. The comparison may in addition to the qualitative leak indication also quantify the leak flow by dividing the difference in gas volume with the breath cycle duration.

The leak detection interval is minimum one breath cycle comprising inspiration and expiration phases. The interval may also comprise a number of successive breath cycles to provide better rejection of artifacts in leak identification. This may occur for example if the bellows 15 is not at the top position at the end of expiration, and is filling during the breath cycle. Such change in the anesthesia system volume is not revealed by the pressure measurement of the pressure sensor 43, since the PEEP pressure remains unchanged. Integrating the leak over multitude of breaths would improve the specificity of the leak detection. Alternatively, a position of the bellows 15 inside the bottle 14 must be indicated to the leak analyzer 40 by using the specific sensor 44.

Further the leak analyzer 40 can be provided with the information about changes in the positive end-expiratory pressure (PEEP), because those changes may result in erroneous leak detections.

The leak analyzer 40 can also determine the differences in inspired- and expired patient gas volumes using the patient flow signal of the signal line 105 from the patient flow sensor 29, because both the patient inspiration- and expiration gases are flowing through this sensor. This difference can be used to identify whether the system leakage is located on the breathing circuit 2 or between the breathing circuit 2 and the subject 4 where the most likely site for leak is the connection of the endotracheal tube 28 and the subject airways whereas the breathing circuit 2 has many potentially leaking connections.

As described above the signal of the signal line 104 from the flow sensor 38 of the gas mixer 3 can be exploited by the leak analyzer 40, but this signal can be replaced by at least two or in most cases three different signals of the gas mixer 3. One of them being a signal from the flow sensor 35 to the leak analyzer 40 along a signal line 108, another one being a signal of the signal line 107 from the flow sensor 36 and the third one being the signal of the signal line 109 from the anesthetic agent supply 37 in case such is used to generate inhaled anesthetic agent. The signals from the flow senor 35 indicative of the gas volume flowing from the gas supply 5 or the gas supply 31, the flow sensor 36 indicative of the gas volume flowing from the gas supply 30 and the anesthetic agent supply 37 indicative of the gas volume vaporized are used by the leak analyzer 40 to determine the whole gas volume from the gas mixer 3.

FIG. 2 presents another embodiment of the leak detection in the anesthesia system. The reciprocating unit 6 comprising a long gas flow channel 41 functions differently from the one shown in FIG. 1. The channel 41 is part of a continuous flow pathway between said gas supply 5 and said breathing circuit 2. The separation of the ventilator gas and the breathing gas is made with a gas gradient reciprocating in the gas flow channel 41. In this the receiving information indicative of the measured gas flows the gas supply 5 pushes the inspiration gas towards the ventilator 1 and through the flow control valve 7 to control the inspired gas flow and through the flow sensor 8 for measuring the flow and to the channel 41. This will push the prevailing gas from the channel 41 further to the inspiration tube 18 of the breathing circuit 2 and further to the subject 4. During the expiration the expiration valve 9 is opened releasing the pressure of the channel 41 and the breathing circuit 2. The lung compliance drives the gas out from the lungs through expiration tube 19 to the channel 41. This pushes the gas loaded into the ventilator end of the channel 41 during the inspiration out from the channel 41 through the expiration valve 9 and the flow sensor 10 of the ventilator 1. Would the fresh gas stream into the breathing circuit 2 exceed the one removed, the excess flows through the channel 41 of the reciprocating unit 6 and gets also scavenged through the expiration valve 9 and becomes measured with the flow sensor 10. Thus separate scavenging flow sensor is not needed in this embodiment.

Instead of using in FIG. 2 embodiment two separate flow sensors, which are the flow sensor 8 to measure the ventilator gas flow from the gas supply 5 added for the inspiration gas flow and the flow sensor 10 to measure the ventilator gas flow removed for the expiration and which was released by the expiration valve 9, only one sensor can be used to replace it when it is put in a place where these flows can be observed and one suitable place for such flow sensor 42 is in the reciprocating unit 6. A good place for the pressure sensor 43 in FIG. 2 embodiment is between the reciprocating unit 6 and the expiration valve 9, but as well other parts of the anesthesia system e.g. in the breathing circuit 2 or in the endotracheal tube 28 are possible places for the pressure sensor 43. Otherwise the embodiment of FIG. 2 is used on the same principles as described above in connection to FIG. 1. The gas mixer 3 and the breathing circuit 2 can be identical to FIG. 1.

A signal line 110 is needed, maybe instead of signal lines 101, 102 in an embodiment of FIG. 2 in case upstream the reciprocating unit 6 exists the flow sensor 42 to measure both the ventilator gas flow added for the inspiration and the gas flow removed for the expiration. The signal line 110 extends from the flow sensor 42 to the leak analyzer 40 receiving information indicative of the measured gas flows. Further the leak analyzer 40 can work in the same principle as explained with FIG. 1.

The written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for detecting a leak in an anesthesia system, the method comprising:
   controlling respiratory movements by means of ventilator gas flows;
   measuring the ventilator gas flow added for an inspiration and removed for an expiration;
   supplying a fresh gas flow for a respiration;
   measuring the fresh gas flow added for the respiration;
   receiving information indicative of the measured gas flows;
   determining based on said received information both the gas volume added and the gas volume removed;
   comparing these determined gas volumes to each other; and
   determining based on comparing the anesthesia system leakage.

2. The method according to claim 1, wherein controlling respiratory movements by means of ventilator gas flows includes supplying gas flow for the inspiration and also includes removing gas flow for the expiration.

3. The method according to claim 1, wherein supplying a fresh gas for an inhalation includes an anesthetic agent vaporized and a gas flow of the anesthetic agent vaporized is measured either together with other fresh gas flow or separately.

4. The method according to claim 1, further comprising:
   receiving information indicative of known gas flow which can be one of an anesthetic agent vaporized among the fresh gas flow and a gas flow withdrawn for analyzing.

5. The method according to claim 1, further comprising:
   measuring a total gas flow of the inspiration exploiting a single measurement and measuring the total gas flow of the expiration exploiting also a single measurement.

6. The method according to claim 1, further comprising:
   (i) analyzing gas flow; or
   (ii) analyzing gas flow, said analyzing comprising withdrawing analyzed gas from the anesthesia system, wherein information regarding the withdrawn gas is part of the receiving information indicative of the measured gas flows.

7. An arrangement for detecting a leak in an anesthesia system, the arrangement comprising:
   a ventilator configured to control respiratory movements, including at least one flow sensor for measuring a ventilator gas flow added for an inspiration and removed for an expiration;
   a gas mixer for supplying a fresh gas flow for a respiration, including at least one flow sensor for measuring the fresh gas flow added;
   a breathing circuit configured to conduct an expiration gas flow to said ventilator and to conduct the fresh gas flow from said gas mixer for the respiration and to conduct the ventilator gas flow added for the inspiration;
   a leak analyzer configured to receive information indicative of the measured gas flows of said flow sensors, wherein the leak analyzer is configured to determine based on said information both the gas volume added and the gas volume removed and to compare these gas volumes to each other and to determine the anesthesia system leakage.

8. The arrangement according to claim 7, further comprising:
   a patient flow sensor configured to measure a total gas flow of the inspiration and the expiration, the flow sensor located in a patient tube of said breathing circuit.

9. The arrangement according to claim 7, wherein the ventilator is connectable to a gas supply and includes a reciprocating, unit configured to guide respiratory movements, the reciprocating unit comprising:
- a bellows in a bottle separating a gas flow between said gas supply and said breathing circuit, and
- a sensor configured to indicate a position of the bellows inside the bottle, wherein information from the sensor together with other received information transmitted to the leak analyzer is used when determining the anesthesia system leakage.

10. The arrangement according to claim 7, further comprising:
- a pressure sensor configured to measure a positive end-expiratory pressure (PEEP) and inform a change in the pressure between breaths to the leak analyzer when determining the anesthesia system leakage.

11. The arrangement according to claim 7, wherein the gas mixer includes an anesthetic agent supply configured to vaporize an anesthetic agent into the fresh gas flow, and wherein information indicative of the measured or known gas flow of said anesthetic agent supply is received by said leak analyzer.

12. The arrangement according to claim 7, further comprising a gas analyzer configured to analyze gas flow and withdraw a sample of the gas flow, wherein information indicative of the measured or known gas flow of said gas analyzer is received by said leak analyzer.

13. An arrangement for detecting a leak in an anesthesia system, the arrangement comprising:
- a ventilator connectable to a gas supply, and including a reciprocating unit configured to control respiratory movements, and at least one flow sensor for measuring a ventilator gas flow added for an inspiration and removed for an expiration;
- a gas mixer for supplying a fresh gas flow for a respiration, including at least one flow sensor for measuring the fresh gas flow added;
- a breathing circuit configured to conduct an expiration gas flow to said ventilator and to conduct the fresh gas flow from said gas mixer for the respiration and to conduct the ventilator gas flow added for the inspiration;
- a leak analyzer configured to receive information indicative of the measured gas flows of said flow sensors, wherein the leak analyzer is configured to determine based on said information both the gas volume added and the gas volume removed and to compare these gas volumes to each other and to determine the anesthesia system leakage; and wherein the reciprocating unit comprises a channel that is part of a continuous flow pathway between said gas supply and said breathing circuit.

* * * * *

UNITED STATES PATENT AND TRADEMARK OFFICE
CERTIFICATE OF CORRECTION

PATENT NO. : 8,333,191 B2
APPLICATION NO. : 12/565019
DATED : December 18, 2012
INVENTOR(S) : Heinonen et al.

It is certified that error appears in the above-identified patent and that said Letters Patent is hereby corrected as shown below:

Title Page:

Item (65), under "Prior Publication Data", in Column 1, Lines 1-2, delete " US 2010/0078018 A1   Apr. 1, 2010 " and insert -- US 2010/0078018 A1   Apr. 1, 2010 --, therefor.

Item (58), in Column 1, delete "(58) Field        of        Classification" and insert -- (58) Field of Classification --, therefor.

In the Specifications:

In Column 2, Line 19, delete "endotrahceal" and insert -- endotracheal --, therefor.

In Column 3, Line 57, delete "fort" and insert -- forth --, therefor.

In Column 5, Line 29, delete "L/min." and insert -- mL/min. --, therefor.

In Column 5, Line 32, delete "CO2" and insert -- CO2 --, therefor.

In Column 5, Line 38, delete "L/min." and insert -- mL/min. --, therefor.

In Column 8, Lines 20-21, delete "preberably" and insert -- preferably --, therefor.

In the Claims:

In Column 10, Lines 23-24, in Claim 3, delete "vaporized" and insert -- vaporized, --, therefor.

Signed and Sealed this
Fourteenth Day of May, 2013

Teresa Stanek Rea
*Acting Director of the United States Patent and Trademark Office*

CERTIFICATE OF CORRECTION (continued)
U.S. Pat. No. 8,333,191 B2

In Columns 10 & 11, Line 67 & 1, in Claim 9, delete "reciprocating, unit" and insert -- reciprocating unit --, therefor.